United States Patent
Okada

(10) Patent No.: US 8,409,622 B2
(45) Date of Patent: *Apr. 2, 2013

(54) PROCESS FOR MANUFACTURING BIOCOMPATIBLE MATERIAL

(75) Inventor: Yoshiaki Okada, Tokyo (JP)

(73) Assignee: RBS Co., Ltd., Matsui-Shi Shimane (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/447,832

(22) Filed: Apr. 16, 2012

(65) Prior Publication Data
US 2012/0251626 A1    Oct. 4, 2012

Related U.S. Application Data

(62) Division of application No. 12/255,931, filed on Oct. 22, 2008, now Pat. No. 8,241,671.

(30) Foreign Application Priority Data

Oct. 26, 2007  (JP) .................... 2007-278908

(51) Int. Cl.
*A61K 35/12* (2006.01)
*A61K 33/00* (2006.01)
*C07K 1/14* (2006.01)
*A61K 33/06* (2006.01)
*A61K 33/42* (2006.01)
*A61K 38/00* (2006.01)
*C07K 14/78* (2006.01)

(52) U.S. Cl. ........ 424/520; 424/600; 424/605; 424/606; 424/682; 435/273; 514/16.9; 530/427

(58) Field of Classification Search .................. None
See application file for complete search history.

(56) References Cited

U.S. PATENT DOCUMENTS 8,241,671 B2 *  8/2012  Okada .................... 424/520

FOREIGN PATENT DOCUMENTS

| JP | 1993155900 | 6/1993 |
| JP | 2001211895 | 8/2001 |
| JP | 2003238598 | 8/2003 |
| JP | 2003327599 | 11/2003 |
| KR | 2004074598 A | 8/2004 |

OTHER PUBLICATIONS

Sankar, S. et al "Preparation and Partial Characterization of Collagen Sheet from Fish (*Lates calcarifer*) Scales" International Journal of Biological Macromolecules, Jan 2008 (published online Aug. 26, 2007) 42(1) pp. 6-9.

Takenaka, Atsushi; Okada, Akira; Iwai, Kenta; Ayaki, Yoshikazu "Separation of Collagen from Fish Scales by Treatment of Dilute Hydrochloric Acid Aqueous Solution" Nippon Shokuhin Kaqaku Koqaku Kaishi, 2003,50(2),pp. 67-71. (Abstract only).

Lanzing, WJR "The Fine Structure of Fins and Finrays of *Talapia mossambica* (Peters)" Cell Tiss. Res., 1976, 173(3),pp. 349-356.

* cited by examiner

*Primary Examiner* — Chris R Tate
*Assistant Examiner* — Aaron J Kosar
(74) *Attorney, Agent, or Firm* — Notaro, Michalos & Zaccaria P.C.

(57) ABSTRACT

A process for producing a biocompatible material includes the steps of mixing an extract of a fish scale-derived hydroxyapatite (with water content of 70 to 75% by weight) and of a fish scale-derived collagen (with water content of 40 to 60% by weight) in the weight percent ratio of about 8:2, stirring the mixture and drying the mixture by a hot blast in order to obtain a composite.

3 Claims, 9 Drawing Sheets

Hydroxyapatite/Collagen Mixture

↓x 2,000    ↓ x 10,000

↑x 270    ↑ x 20,000

Composite

↓ x 2,000    ↓ x 10,000

↑ x 270    ↑ x 20,000

Solely Hydroxyapatite

↓ x 2,000 ↓ x 10,000

↑ x 100 ↑ x 20,000

Distal Epiphysis (A)

OVX control · Composite

Diaphysis (B)

OVX control · Composite

Traverse Cross Sectional Image

OVX                                   Sham

Longitudinal Cross Sectional Image

OVX                                   Sham

PROCESS FOR MANUFACTURING BIOCOMPATIBLE MATERIAL

CROSS REFERENCE TO RELATED APPLICATION

This is a divisional of application Ser. No. 12/255,931 filed Oct. 22, 2008 which is incorporated here by reference and which claims priority on Japanese application no. 2007-278908 filed Oct. 26, 2007, which priority claim is repeated here.

FIELD OF THE INVENTION

The present invention relates to a process for manufacturing of a biocompatible material using fish scales, which is so prepared that it can be easily absorbed to organisms such as mammals.

BACKGROUND ART

Calcium is an important component which forms human bones and tooth. It is further known that the substance is essential also in the cardiovascular and neurotransmission. Furthermore, it is well-known that collagen exists in almost all tissues including human bones, cartilages, tooth, skin, vessels and organs, and in other words, it is an essential component which is indispensable for organization of human body. However, due to decrease of the calcium and collagen for various reasons, so-called aging symptoms such as osteoporosis and hypometabolism become obvious.

Hydroxyapatite is a common designation for inorganic chemicals consisting mainly of calcium and phosphoric acids and expressed by a formula $Ca_{10}(PO_4)_6(OH)_2$. It is a main component of bones and tooth. Concerning a process for manufacturing, the hydroxyapatite the one using fish scale has been proposed. As a prior art document which describes the process for manufacturing the fish scale-derived hydroxyapatite, there is a disclosure in JP Laid-Open 2001-211895.

On the other hand, collagen belongs to proteins and is often extracted from collagen tissues of mammals like a cow and a pig. However, these mammals are always facing a risk of infection of pathogens such as prions which are eliminated with difficulties using ordinary sterilization and pasteurization methods, thus a manufacture of collagen from fish which are free from such fear. A fish skin is used in the manufacture of collagen from fish, a problem is raised that the collagen from the fish skin smells like fish and generates white turbidity leading to a low permeability. Therefore, several processes for manufacturing collagen from fish scale, wherein the processes can contribute to a solution for fish-like smells particular to fish, have been proposed. As prior art documents which describe the process for manufacturing collagen from the fish scale, there are disclosures in JP Laid-Open Patent Publications H05-155900, 2001-327599 and 2003-238598.

It is known that the hydroxyapatite as above described or the traditional calcium are, though poorly absorbed by a human body, biocompatible, and further, once absorbed by a human body, these substances can supplement these components that are deficient inside a human body. Starting from this common knowledge, the inventors have devotedly studied in order to facilitate a digestion and absorption by a human body, so that they have finally found out that, although calcium has conventionally been considered as showing a poor absorption, the collagen is assigned a scaffolding function by forming a composite from the hydroxyapatite and collagen, so that the hydroxyapatite absorbed on the collagen is well absorbed by a human body. Based on these findings, the inventors have then elaborated the present invention.

SUMMARY OF THE INVENTION

The present invention has an object to provide a process for manufacturing a biocompatible material consisting mainly of a fish scale-derived hydroxyapatite and a fish scale-derived collagen which material is digested and absorbed by a human body in a manner as easy as possible.

To achieve the above-mentioned object, this invention is characterized in that in obtaining the above-mentioned composite, an extract of a fish scale-derived hydroxyapatite (with water content of 70 to 75% by weight) and the one of a fish scale-derived collagen (with water content of 40 to 60% by weight) are mixed in the weight percent ratio of about 8:2 and then stirred, and after that the mixture is dried by hot blast in order to obtain the composite.

Further, this invention is characterized in that a production of the composite is incorporated in the process for producing the fish scale-derived hydroxyapatite.

Still further, this invention is characterized in that a production of the composite is incorporated in the process for producing the fish scale-derived collagen.

As above described, in a process for producing a biocompatible material according to the present invention, it is characterized in that the material is safe as it is made of a fish scale, and that the composite is formed by mixing respective extracts of the hydroxyapatite and of the collagen, stirring and depositing the mixture, so that the collagen is absorbed and bonded in gaps between crystal structures of hydroxyapatite, which assigns a scaffolding function to the collagen contained in the composite and more easily realizes an absorption by a human body of the hydroxyapatite absorbed on the collagen. Further, in view of the present circumstances where the calcium intake of the Japanese falls below the nutritional allowance and those affected by osteoporosis increase yearly due to an insufficient calcium intake during the meal and decrease in calcium absorbing ability accompanied by ageing, etc., the present invention is effective as a solution for the problematic situation.

DETAILED DESCRIPTION OF THE EXAMPLES

Hereinafter reference is made to the case where a production of a biocompatible material according to the present invention is incorporated into a production process of hydroxyapatite, but it may be also incorporated into a production process of collagen, which is described below.

Figure 1:
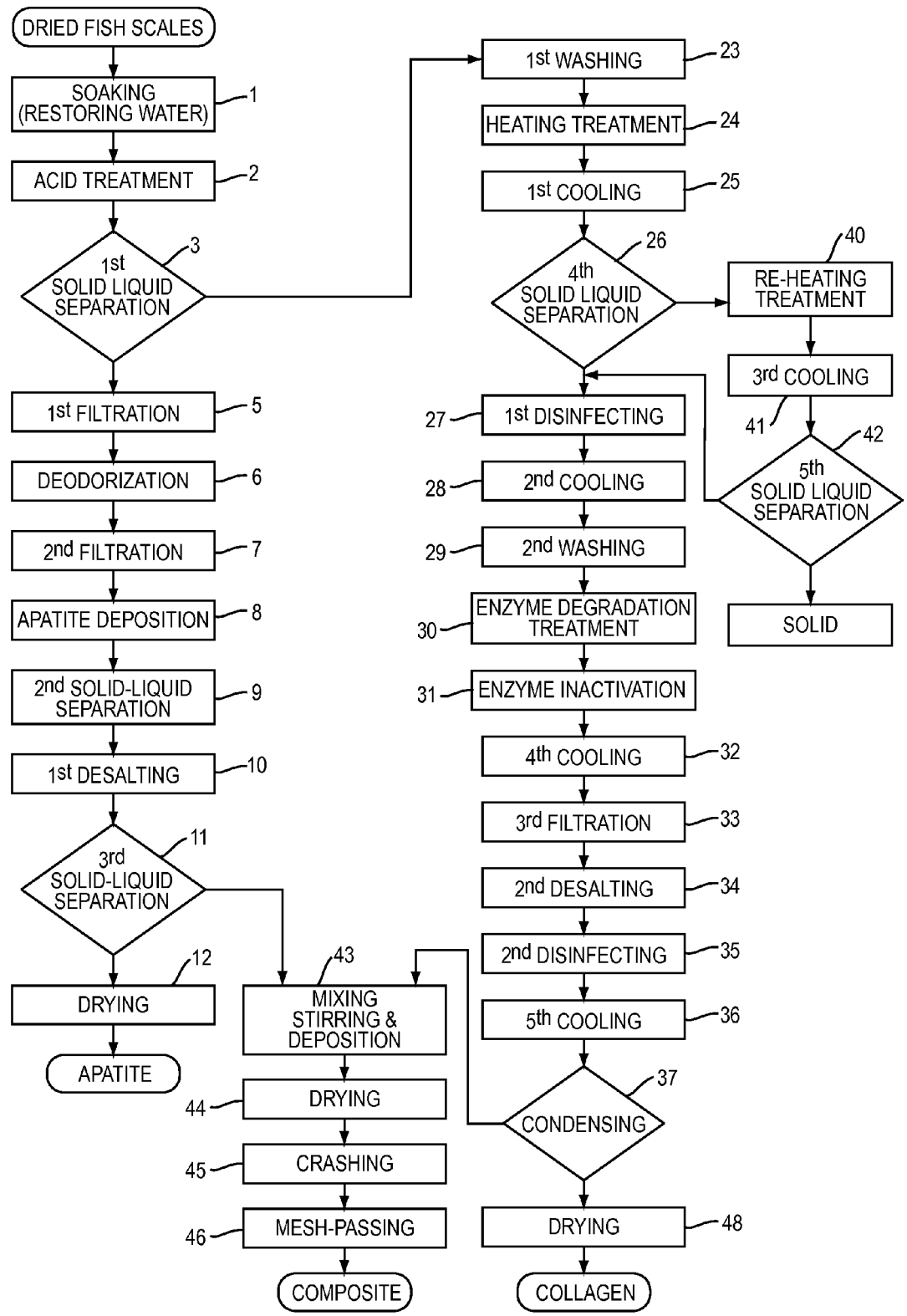
FIG. 1 is a flowchart diagram showing an example of process for producing a hydroxyapatite/collagen composite according to the present invention.

FIG. 1 is, as above stated, a flowchart diagram showing an example of process for producing a composite, focused on the production line of hydroxyapatite. As shown on the Figure, the process for producing the composite according to Example 1 comprises a soaking step 1 for soaking dried fish scales in water, and an acid treatment step 2 for subjecting to acid treatment the fish scales which has been previously soaked in water and then drained, by soaking them in an acidic aqueous solution at 15 to 35° C. for 10 to 30 minutes so as to extract hydroxyapatite contained in the fish scales, and a first solid-liquid separation step 3 for separating a hydroxyapatite extract containing solid resultant from the acid treatment step 2 into solid and liquid. The liquid separated during the first solid-liquid separation step 3 then proceed to a first filtration step 5, while the solid (decalcified fish scales) is transferred to a first washing process 23 of a process for producing collagen, so that collagen can be produced from the solid.

Fish scales are not particularly limited, and their selection may be made indifferent to fish types, e.g. whether they are of sea fish or freshwater fish, but includes scales of carp, tilapia, Japanese seaperch, true sardine, sea bream, salmon, Japanese horse mackerel, etc., and in particular those of carp, tilapia, Japanese seaperch, etc. are preferable in view of hydroxyapatite and collagen content and a relatively greater availability. However, the fish scales used in practice may be a mixture of various fish scales. Further, the fish scales may be dried or undried, but in particular dried fish scales are preferable in view of comfort in handling. In using dried fish scales, they are subjected to a soaking (water treatment) step for soaking them in water prior to an acid treatment so that they restore their original water content. In the present example dried fish scales are used.

In a soaking step 1 dried fish scales are soaked in water so that they restore their original water content as above mentioned, and the original water content is restored e.g. by placing a permeable nylon net filled with dried fish scales into a tank with water of an amount of 2.5 to 4.0 times as much as the dried fish scales, and thus soaking the dried fish scales in water for 10 to 14 hours. A nylon net of mesh size of 1 mm or less is preferably selected. The dried fish scales which have undergone the soaking step 1 are drained and then proceed to a subsequent acid treatment step 2.

In the acid treatment step 2 ash consisting mainly of hydroxyapatite is separated from dried fish scales. Drained fish scales are removed from a nylon net, and then placed into an acidic aqueous solution, so that the above-mentioned ash content is separated from the above-mentioned fish scales. The acidic aqueous solution is not particularly limited, but may be an organic acid aqueous solution or a mineral acid aqueous solution, and in particular a hydrochloric acid aqueous solution is preferable. In the hydrochloric acid aqueous solution preferred conditions vary according to fish scale type, but e.g. the solution is preferably produced by pouring a hydrochloric acid of purity of 35% (of 65 wt % with regard to the fish scales, and of a hydrochloric acid concentration of 5.7%) into water of an amount of 2.5 to 4.0 times as much as the fish scales.

A soaking duration during which fish scales are soaked in an acidic aqueous solution for an acid treatment varies according to fish scale type, and is preferably e.g. 10 to 30 minutes, and in particular preferably 15 minutes under a hydrochloric acid concentration of a hydrochloric acid aqueous solution of the preceding paragraph. During the duration the mixture is stirred using a stirrer. If the soaking duration is less than 10 minutes, the fish scales are not sufficiently decalcified and a yield of hydroxyapatite turns out low. On the other hand, there is little need to arrange a soaking duration more than 30 minutes. Furthermore, a temperature of the acid aqueous solution is not particularly limited, but e.g. preferably 15 to 30° C., and more preferably 25° C. (±5° C.). Under the conditions for hydrochloric acid concentration of the above-described hydrochloric acid aqueous solution and soaking duration, fish scales are not sufficiently decalcified in a temperature below 15° C. and a yield of hydroxyapatite turns out low, while over 30° C., a yield of collagen turns out low. In conducting the acid treatment, fish scales are preferably stirred while soaked in the acid aqueous solution. A means for stirring is not particularly limited, a spatula, etc. may be selected other than a stirrer. Once fish scales have undergone the acid treatment step 2, they are subsequently transferred to a first solid-liquid separation step 3.

In the first solid-liquid separation step 3 a solid content of fish scales is separated using a vibrating sieve, etc. from a treated extract subjected to an acid treatment step 2, wherein the solid content separated during this step is transferred to a collagen production step, while the treated extract containing hydroxyapatite (ash) to a first filtration step 5, during which the extract is filtrated.

The first filtration step 5 is arranged for removing particulate foreign substance from hydroxyapatite extract, and conducted e.g. using a woven wire product. A mesh scale of the woven wire product is not particularly limited, but 20-200 is preferably selected. The hydroxyapatite extract filtrated during this first filtration step 5 is subsequently deodorized during a deodorization step 6.

A deodorization treatment during the deodorization step 6 is not particularly limited, but may be conducted e.g. using activated carbon. In using the activated carbon, the amount equivalent to 1.5% of hydroxyapatite extract is preferably selected. The deodorization treatment may be conducted e.g. using woody or palm-chip activated carbon. The hydroxyapatite extract after the deodorization treatment is further filtrated during a second filtration step 7.

A method for filtration in the second filtration step 7 is not particularly limited, but an apparatus for filtration may be also used, wherein diatomaceous earth is placed into a hydroxyapatite extract, and a resultant liquid is stirred and at the same time filtrated through a filter fabrics coated with diatomaceous earth. The acid-treated liquid after the filtration is subsequently subjected to a treatment for apatite deposition during an apatite deposition step 8.

A treatment for deposition during the apatite deposition step 8 is conducted for depositing hydroxyapatite by adding an alkali to a hydroxyapatite extract. The alkali is not particularly limited, but includes sodium hydrate, potassium hydrate, etc. The method for adding the alkali is not particularly limited. When the alkali is added to the hydroxyapatite extract and stirred until pH turns out to be 6 to 9, hydroxyapatite is deposited. The deposited hydroxyapatite is subsequently separated from the liquid in a second solid-liquid separation step 9. In the meantime, hydroxyapatite is herein deposited by adding an alkali, but an alkali aqueous solution in place of an alkali may be added for depositing hydroxyapatite.

In the second solid-liquid separation step 9 a deposited hydroxyapatite is separated from a remaining liquid, and the means is not particularly limited provided that the solid can be separated from the liquid, but a filter press, a centrifuge etc. may be used for this purpose.

Hydroxyapatite separated from a liquid during the above-mentioned second solid-liquid separation step 9 is subsequently collected into a tank, desalted during a first desalting step 10, and again separated from a liquid a third solid-liquid separation step 11. The resulting product is mixed to a collagen extract after an adjustment in moisture. A manner of the above-mentioned first desalting step 10 is not particularly limited, an ion exchanger, etc. may be used during this step for removing sodium ion contained in the liquid, but a desalting treatment may be also conducted by washing with water. In desalting through this washing step, production costs can be reduced.

A collagen extract is preferably produced, as above described, based on acid-treated fish scales separated from a liquid during a first solid-liquid separation step 3 of a production line of hydroxyapatite and following production steps to be described.

It is characterized in that water is added to fish scales separated from a liquid during a first solid-liquid separation step 3 which are subjected to a pH adjustment during a first washing step 23, and fish scales in water comprise the following steps: a heating treatment step 24 for extracting collagen contained in the fish scales, a first cooling step 25 for cooling to a room temperature a heated liquid containing a solid from the heating treatment step 24, a forth solid-liquid separation step 26 for separating a solid from a collagen extract cooled during the first cooling step 25, a first disinfecting step 27 for heating and disinfecting the collagen extract separated during the forth solid-liquid separation step 26, a second cooling step 28 for cooling to a room temperature the collagen extract disinfected under heat during the first disinfecting step 27, a second washing step 29 for adjusting pH of the collagen extract cooled during the second cooling step 28, and an enzymatic degradation step 30 for enzymatically degrading the collagen extract of which pH is adjusted by adding an enzyme. In the meantime, the fish scales separated from a liquid during the forth solid-liquid separation step 26 are again heated during a reheating treatment step 40 in order to extract a collagen, and following a third cooling step 41 a collagen extract is again separated during a fifth solid-liquid separation step 42 and the resultant product is added to the collagen extract obtained during the above-mentioned forth solid-liquid separation step 25, so that the fish scales can be consumed without waste.

A collagen extract cooled after a heating treatment and then separated from solid is subjected to a disinfecting treatment during a first disinfecting step. The disinfecting treatment is not particularly limited, but a heated liquid may also be heated to 70 to 80° C., preferably to 75° C. The heated liquid after the disinfecting treatment is cooled during a second cooling step 28 to a temperature at which an enzyme can be activated, e.g. 60° C., to be described below, and then its pH is adjusted during a second washing step 29 to 5 to 8, in particular 6.5 (±0.2). The adjustment in pH is not particularly limited, but may be conducted by adding an alkali, such as sodium hydrate, potassium hydrate, etc. The collagen extract of which pH has been adjusted during the second washing step 29 is subjected to a treatment under a subsequent enzymatic degradation step 30.

The enzymatic degradation step 30 is for adding an enzyme to a collagen extract subjected to a treatment with regard to pH during a second washing step 29, so that a molecular weight of collagen can be reduced. The enzymatic degradation treatment is conducted in order to obtain a collagen of a molecular weight of 500 to 3000, more preferably of 500 to 2000, and most preferably of 500 to 1000. An enzyme is not particularly limited provided that the heated liquid can be enzymatically degraded, but includes e.g. an alkaline enzyme derived from *Bacillus licheniformis* (Genencor Int. Inc., trade name: Protex 6L), etc. An addition amount of the enzyme is not particularly limited, but is preferably 0.01 to 0.1%, more preferably 0.08% of the substrate.

A temperature for enzymatic degradation varies according to enzyme, but is preferably 30 to 70° C., more preferably 60° C. A duration for enzymatic degradation varies according to enzyme, but is preferably 3 to 10 hours, more preferably 6 to 8 hours, most preferably 8 hours. If the duration for enzymatic degradation is less than 6 hours, a desired reduction in molecular weight of collagen cannot be sufficiently realized, while under a duration for enzymatic degradation more than 10 hours the molecular weight of collagen remains unchanged. Furthermore, the enzymatic degradation treatment is preferably conducted with stirring. A method for the stirring is not particularly limited, but e.g. a stirrer, etc. may be selected for this purpose.

In a collagen extract treated during an enzymatic degradation step 30 (it may be referred to as enzyme-treated liquid) an enzyme is subsequently deactivated by heating the extract in an enzyme deactivation step 31 at 80 to 85° C., more preferably at 85° C. for 15 minutes. A liquid with a deactivated enzyme is cooled following a forth cooling step 32 to e.g. 60° C. Following the cooling treatment, a solid is removed from an enzyme-treated liquid during a third filtration step 33. The third filtration step 33 is not particularly limited provided that the solid can be removed, but e.g. a clarifying filtration etc. using a filter press is preferable. For clarifying filtration a filtration apparatus etc. may be used, in which a diatomaceous earth is placed into the enzyme-treated liquid, and the resulting liquid is stirred and at the same time filtrated through a filter fabrics coated with diatomaceous earth. Furthermore, a deodorizing treatment is preferably conducted during the third filtration step 33. In the deodorizing treatment, a woody or palm-chip activated carbon e.g. may be used.

Salt contained in a filtrate after a clarifying filtration (it may be referred to as treated liquid) is removed from the treated liquid during a second desalting step 34. The desalting treatment is not particularly limited, and e.g. sodium ion contained in the liquid may be removed using an ion exchanger, but the desalting treatment may also be conducted by washing. Production costs can be reduced by desalting with this washing step. From this desalting step as above described, a tasteless and odorless collagen is obtained. The desalted treated liquid is, following a disinfecting treatment during a second disinfecting step 35 e.g. by heating at 120° C. for 3 seconds, then cooled during a fifth cooling step 36 to e.g. 75° C. or less. The cooled treated liquid is condensed during a condensing step 37, so that it reaches 40° Bx (±1.0° Bx) at an evaporation temperature of 60 to 65° C. By this treatment a collagen extract is obtained.

The collagen extract with water adjustment is added to the above-described hydroxyapatite extract with water adjustment in the weight ratio of about 80% by weight of hydroxyapatite to about 20% by weight of collagen, both being calculated based on the solid content, so that the mixture is stirred and mixed during a stirring and depositing step 43. As at this point the collagen is deposited in the hydroxyapatite, the deposited and bonded product is subsequently dried during a drying step 44, so that a solid hydroxyapatite/collagen composite is ready. The composite is then crushed during a crushing step 45 and further subjected to a mesh-passing step 46 during which the composite is mesh-passed, so that pulverized hydroxyapatite/collagen composite can be obtained.

Figure 2:
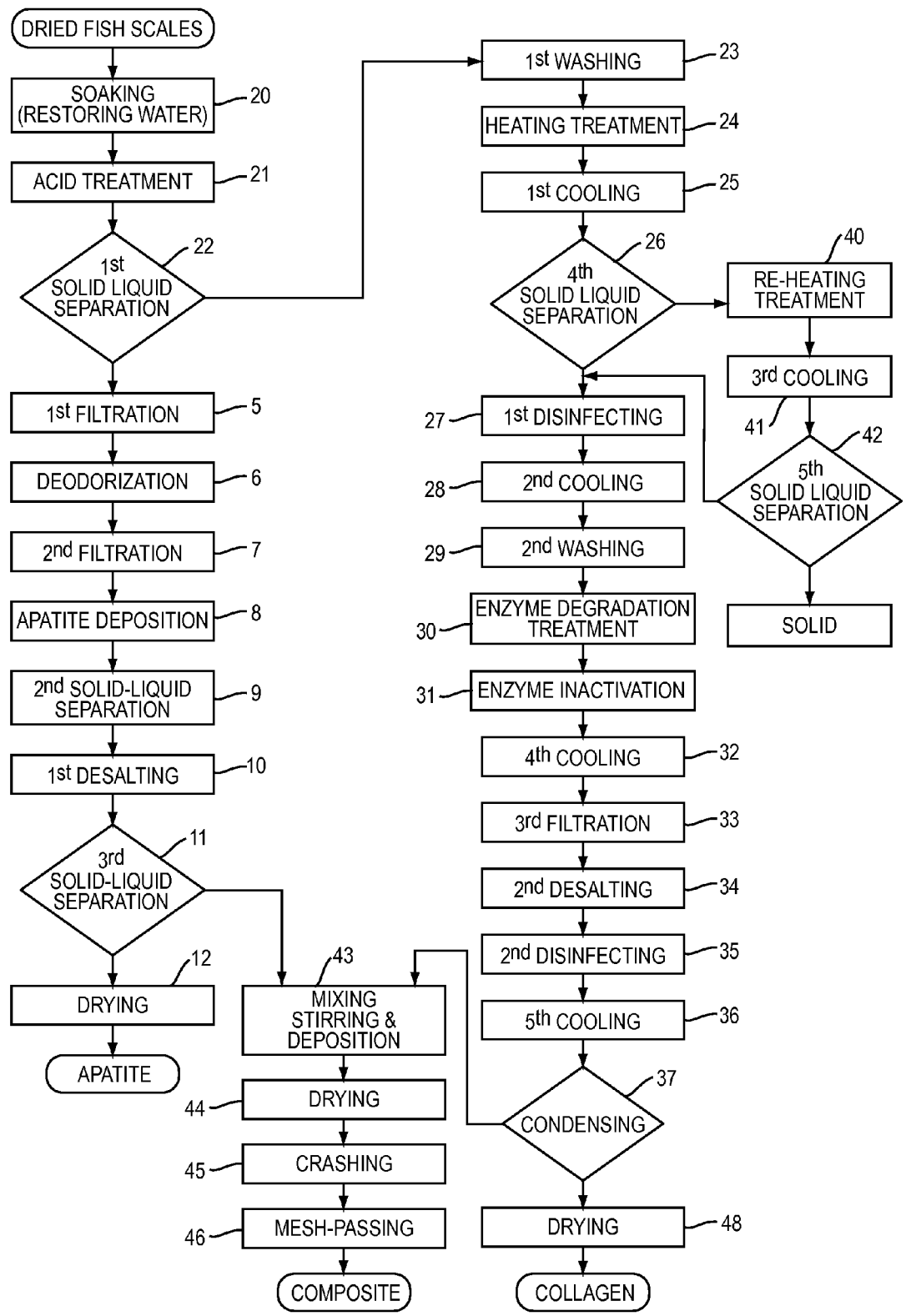
FIG. 2 is a flowchart diagram showing another example of process for producing a hydroxyapatite/collagen composite according to the present invention.

In the meantime, reference has been made in the foregoing to the case where steps for producing collagen extract are separated from those for producing hydroxyapatite, however, the process for producing the collagen is identical to that for hydroxyapatite up to a point where dried fish scales restore the original water content and then are treated by acid. To that point therefore the both processes undergo identical steps, so that, needless to say, focus can also be placed on the production line for the collagen within a overall production line, and in particular a production process as follows is also possible: the dried fish scales are allowed to restore their original water content during a soaking step 20 and then are treated by acid during an acid treatment step 21, before hydroxyapatite extract is separated and the subsequent steps concerning hydroxyapatite is separated for its own production line, as shown in FIG. 2. The above-mentioned production process is shown in FIG. 2, and steps with identical reference numerals are identical to those in FIG. 1, therefore references thereto are omitted.

Thereafter, in obtaining a substance of fine-powdered hydroxyapatite from the above-mentioned hydroxyapatite extract, the extract is dried during a drying step 12, in particular as shown in FIG. 1. The drying step 12 is not particularly limited provided that the hydroxyapatite extract can be dried, but may be dried e.g. using hot blast. A temperature of the hot blast is not particularly limited, but is preferably 65 to 100° C., and more preferably 75° C. A duration for drying is not particularly limited, but preferably 15 to 24 hours, and more preferably 18 hours. After this step, dried fine-powdered hydroxyapatite can be obtained.

Subsequently, in obtaining a simple substance of fine-powdered collagen from the above-mentioned collagen extract, a condensed collagen extract is subjected to a drying step 48 wherein it is freeze-dried or otherwise dried using methods including spray drying so that dried fine-powdered collagen can be obtained.

Fine-powdered collagen obtained in the above-described manner is a tasteless, odorless, high-quality and low molecular weight collagen, of a molecular weight of 500 to 1,000. Collagen contains a large amount of amino acids, and its features vary depending on a composition of these amino acids. In collagen the amino acid composition and sequence are unique in comparison to other proteins, in that three polypeptide chains form clockwise helices respectively, thus keep a stable structure. Further a stable helical structure peculiar to collagen would not be formed without hydroxyproline, and therefore it can be safely stated that the hydroxyproline content is reference value for determining the collagen quality. In other words, collagen containing more hydroxyproline is better in quality. Results are listed in Table 1 from an analysis of a composition of the amino acids contained in the collagen obtained by the process for producing collagen according to the present invention, using the automatic amino acid analysis. All the entries are contents in 100 g of collagen. In the meantime, amino acids are also analyzed, as shown in Table 1, by the automatic amino acid analysis concerning collagen derived from pork skin, collagen of Company A, and collagen of Company B.

TABLE 1

Amino Acid Composition of Collagen
In grams

|  | Present Example | Pork Skin | Company A | Company B |
|---|---|---|---|---|
| Gly | 28.5 | 33.34 | 36.4 | 33.48 |
| Ala | 10.9 | 11.28 | 11.1 | 12.36 |
| Ser | 3.59 | 3.33 | 5 | 3.84 |
| Thr | 2.65 | 1.83 | 2.3 | 2.83 |
| 1/2-cystine | 0.03 | 0 | 0 | 0 |
| Met | 1.55 | 0.47 | 1.5 | 1.52 |
| Val | 2.48 | 2.18 | 1.7 | 2.06 |
| Leu | 2.66 | 2.49 | 2 | 2.14 |
| Ile | 1.35 | 1.08 | 1.1 | 0.92 |
| Phe | 1.84 | 1.26 | 1.2 | 1.32 |
| Tyr | 0.37 | 0.35 | 0 | 0.29 |
| Pro | 13.8 | 12.18 | 11 | 11.59 |
| hydroxyproline | 11.4 | 10 | 6 | 8 |
| Lys | 3.78 | 2.59 | 2.6 | 2.57 |
| His | 0.58 | 0.5 | 0 | 0.5 |
| Arg | 8.58 | 4.7 | 5.1 | 5.16 |
| Asp | 6.15 | 4.32 | 5.5 | 4.14 |
| Glu | 10.4 | 4.57 | 7.8 | 6.97 |
| Trp | 0 | 0 | 0 | 0 |

As seen in Table 1 above, it is observed that collagen produced following a process for producing contains more hydroxyproline than those produced using other materials and following other processes for producing. Moreover, in this collagen reduction to low molecular weight (of a molecular weight of 500 to 1,000) is sought by an enzymatic degradation, so that a biological absorption rate is high.

Subsequently, a powdery hydroxyapatite/collagen composite which is constituent of a biocompatible material according to the present invention is produced as is described below. First concerning the hydroxyapatite extract, 2 kg of dried carp scales is placed into a nylon net of an opening size of 1 mm or less. Then 6.6 kg of water, i.e. 3.3 times as much as the dried fish scales, is poured into a PE (polyethylene) tank and the nylon net stuffed with the dried fish scales is fully soaked in the water in the tank for 12 hours, so that the fish scales restore the original water content.

After the soaking step, water in a PE (polyethylene) tank is once removed and 6.6 kg of fresh water is again poured into the tank. A temperature of the water in the tank is maintained at 20° C. (±2° C.), while 1,300 g of hydrochloric acid having purity 35% is added to the water in order to obtain an aqueous hydrochloric acid solution. An acid treatment is thus conducted by soaking and at the same time stirring the fish scales having the original water content in the aqueous hydrochloric acid solution for 25 minutes. A hydroxyapatite extract obtained by the acid treatment to the fish scales is subjected to solid-liquid separation and then filtered using a filtering apparatus. A filtered hydroxyapatite extract is deodorized using palm-chip activated carbon. After the deodorization treatment the treated liquid is subjected to clarifying filtration using a filter press, so that fine solids are removed from the treated liquid.

Sodium hydroxide (48% by weight NaOH) is added to the filtered hydroxyapatite extract and then the extract is stirred using stirrer so that pH of the extract is adjusted to 7.

Hydroxyapatite is thus eluted by this treatment so that hydroxyapatite particles are deposited. After depositing, the solid is separated from the liquid using a filter press, and then the separated hydroxyapatite is placed into a tank, to which 36 to 48 kg of water i.e. 3 to 4 times as much as the treated liquid is added. The hydroxyapatite is then desalted by stirring the liquid together with the water and thus washing it. Thereafter the liquid is heated to 70° C. and a disinfecting treatment is maintained for 30 minutes, before the liquid is stirred using a filter press for a solid-liquid separation. The hydroxyapatite extract obtained in this manner contains 75% by weight of water and has a weight of 1,800 g.

Subsequently, a collagen extract is produced as is described below. 150 kg of dried carp scales is placed into a nylon net of an opening size of 1 mm or less. Then, the nylon net stuffed with the dried fish scales is placed into a PE (polyethylene) tank containing 495 kL of water, i.e. 3.3 times as much as the dried fish scales and fully soaked in the water in the PE tank for 12 hours, so that the fish scales restore the original water content.

Next 495 kL of water, i.e. 3.3 times as much as the dried fish scales, is poured into another PE (polyethylene) tank and a temperature of the water in the tank is maintained at 20° C. (±2° C.), while 93 kL of hydrochloric acid having purity 35% is added to the water in order to obtain an aqueous hydrochloric acid solution. An acid treatment is thus conducted by soaking and at the same time stirring a nylon net still containing the fish scales having the original water content in the aqueous hydrochloric acid solution for 15 minutes. The nylon net containing the acid-treated fish scales is then unfolded in a washing tank and subjected to 5 washing cycles for 5 minutes, each of the washing cycles being conducted in 600 kL of water so as not to allow the fish scales inside the net to escape outside, so that pH of the fish scales is adjusted to 4.0 (±0.2).

Washed fish scales are then placed into an iron pot containing water eight times as much as the fish scales, and subjected to a first heating treatment which is conducted at 98° C. or higher for 3 hours. This first heating treatment is conducted in order to adjust a final concentration of the liquid at 10 to 12° Bx. If water is evaporated too much and remaining water is less than a desired amount, further water is added. In this case, marks like scales are preferably placed on the iron pot, so that addition of water can be conducted so as to place a water surface each time at a reference mark.

After a first heating treatment a liquid is cooled to 75° C. or lower, and a solid is separated from the liquid in a liquid state after the first heating treatment, using a 2-stage vibrating sieve machine comprising vibrating sieves of 20-200 mesh. Water four times as much as the solid, i.e. fish scales, is added to the solid separated during the solid-liquid separation and then the water containing the solid is subjected to a second heating treatment at 98° C. or higher for 2 hours. This second heating treatment is conducted in order to adjust a final concentration of the liquid at 10 to 12° Bx. If water is evaporated too much and remaining water is less than a desired amount, further water is preferably added.

After a second heating treatment a liquid is cooled to 75° C. or lower, and a solid is separated from the liquid in a liquid state after the second heating treatment, using a 2-stage vibrating sieve machine comprising vibrating sieves of 20-200 mesh. The liquid after the second heating treatment, from which the solid is removed, undergoes a disinfecting treatment at 75° C. for 15 minutes, together with the liquid after a first heating treatment. After the disinfecting treatment the liquid is cooled to 60° C. and enzymatically degraded.

In the enzymatic degradation treatment pH of the heat-treated liquid is first adjusted to 6.5 (±0.2), and after that an alkaline enzyme derived from *Bacillus licheniformis* (Genencor Int., Inc., trade name: Protex 6L) is added to the substrate, 0.08% heat-treated liquid; the liquid containing the enzyme is then stirred at 60° C. (±1° C.) by stirrer for 8 hours.

After the enzymatic degradation treatment the enzymatically degraded liquid (treated liquid) is retained at 85° C. for 10 minutes so that the enzyme is inactivated, and then the treated liquid is cooled to 60° C. After cooling, the treated liquid is deodorized using palm-chip activated carbon and then subjected to clarifying filtration using a filter press, so that the solid contained in the treated liquid is removed. In the meantime, a third filtering step preferably includes a deodorizing treatment. The deodorizing treatment may be conducted e.g. using woody or palm-chip activated carbon. After the solid is removed, the treated liquid is desalted using an ion exchanger. After the desalting treatment, the treated liquid is heated at 120° C. for 3 seconds and thus subjected to a sterilizing treatment, and thereafter it is cooled to 75° C. or lower. The cooled treated liquid is then subjected to a condensing treatment in a condensing tank at 60 to 65° C. in order to adjust to 40° Bx (±1.0° Bx). A collagen extract is obtained in this manner.

Subsequently 1,800 g of hydroxyapatite extract is prepared, which is separated from a solid during a third liquid-solid separation step 11 among steps for producing hydroxyapatite as above described and contains 75% by weight of water, while 220 g of low molecular weight collagen extract is prepared, which is obtained prior to a drying step within the above-described steps for producing collagen and contains 50% by weight of water (the weight for each extract is calculated as solid weight). Thereafter these extracts are altogether placed into a treatment tank, and mixed and stirred in a room temperature for 10 to 20 minutes, so that 2,020 g of deposited and bonded hydroxyapatite/collagen product is deposited. When this deposited and bonded product is then dried under a hot blast atmosphere at 70° C. for 18 hours, 520.6 g of hydroxyapatite/collagen composite with a water content of 5.8% is obtained. The product has a sickly ivory white color and a very weak odor.

In the present example 220 g of low molecular weight collagen extract is prepared, which is obtained within the above-described steps for producing collagen, and more specifically prior to a drying step 48, wherein its water content is adjusted to 50% by weight, while 1,800 g of hydroxyapatite extract is prepared, which is separated from a solid during a third liquid-solid separation step 11 among steps for producing hydroxyapatite as above described, wherein its water content is adjusted to 75% by weight. Thereafter these extracts are altogether placed into a treatment tank, and mixed and stirred in a room temperature for 10 to 20 minutes, so that 2,020 g of deposited and bonded hydroxyapatite/collagen product is deposited. When this deposited and bonded product is then dried during a subsequent drying step under a hot blast atmosphere at 70° C. for 18 hours, 520.6 g of hydroxyapatite/collagen composite with a water content of 5.8% is obtained. The product has a sickly ivory white color and a very weak odor.

Figure 3:
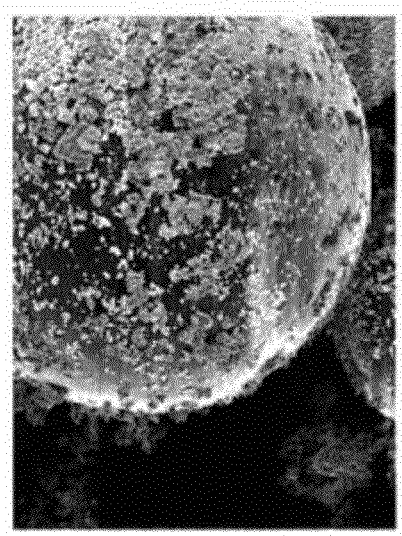
FIG. 3 is an image of a marketed hydroxyapatite/collagen mixture as seen using scanning electron microscope.
Figure 3:
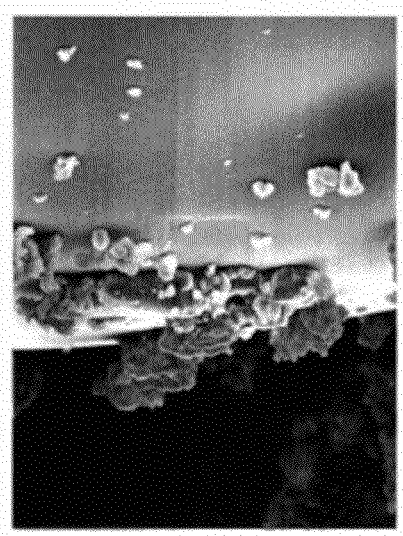
Figure 3:
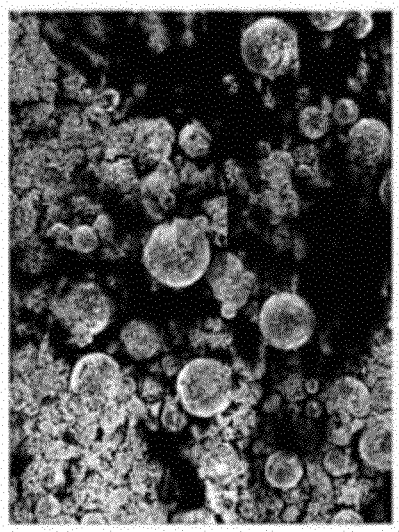
Figure 3:
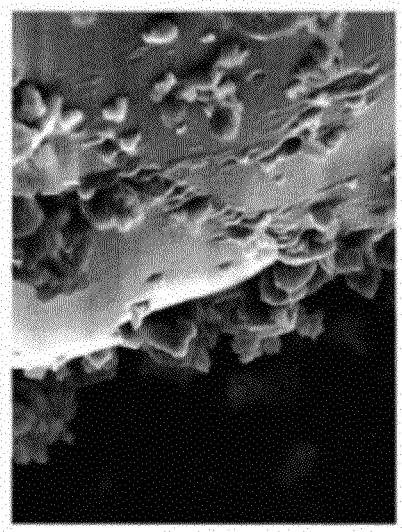
Figure 4:
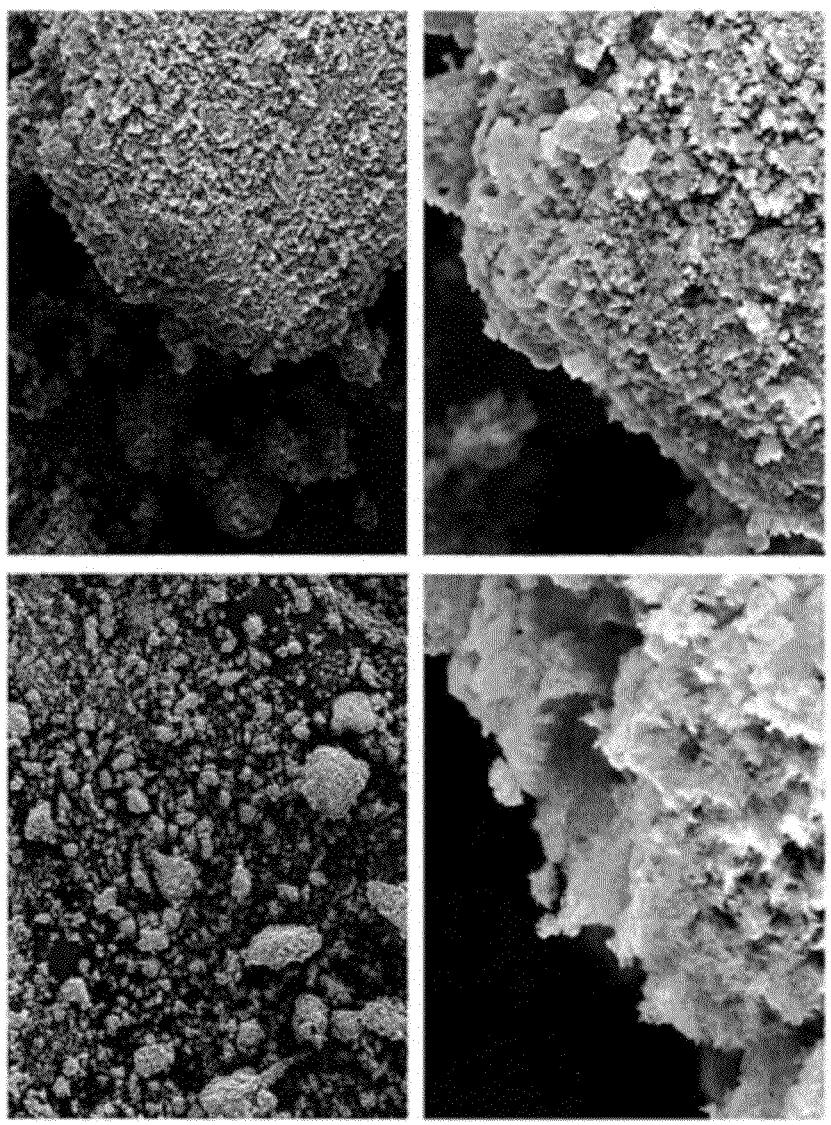
FIG. 4 is an image of a composite which is manufactured according to the present invention, as seen using scanning electron microscope.
Figure 5:
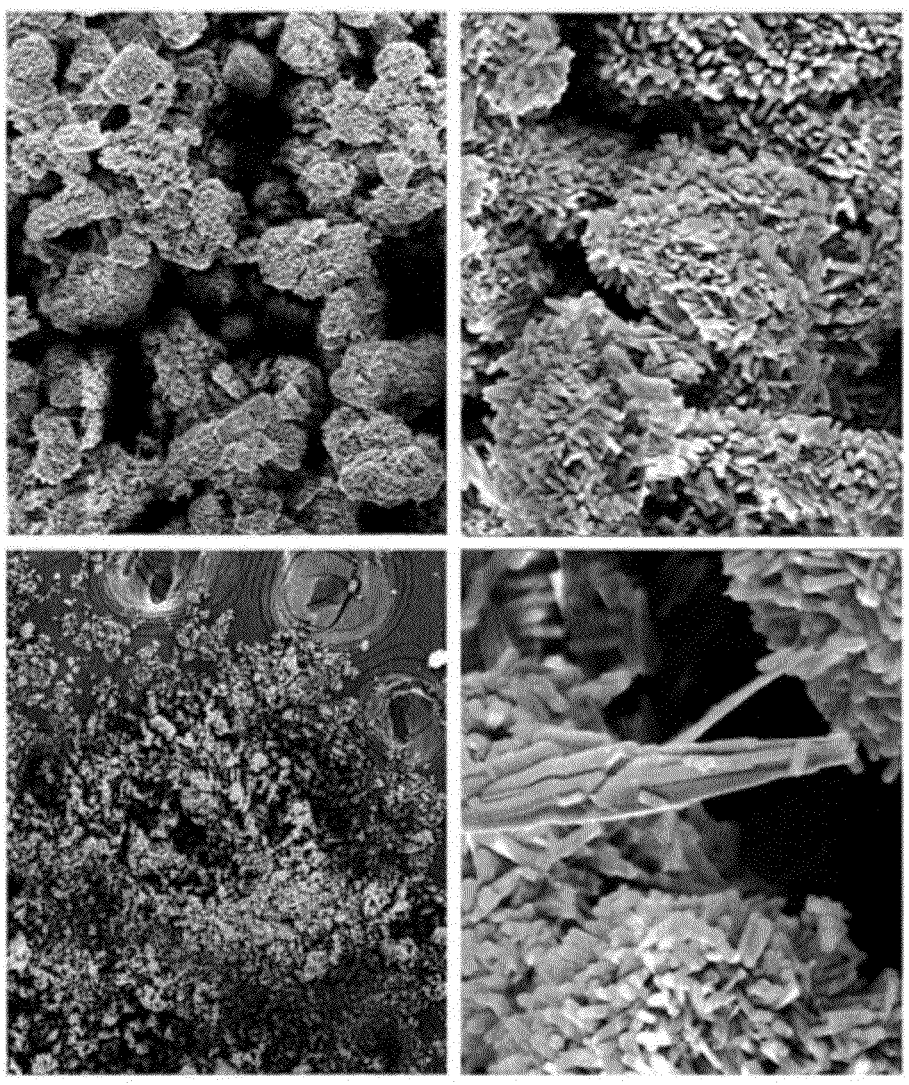
FIG. 5 is an image of a marketed hydroxyapatite as seen using scanning electron microscope.

When a composite obtained in the above-described manner which is then scanned using a scanning electron microscope is compared to a marketed apatite/collagen mixture as scanned using a scanning electron microscope, exclusively amorphous objects are observed in the composite A as shown in FIG. 4, while in the marketed mixture B two types of objects, i.e. spherical objects (collagen) and amorphous objects (hydroxyapatite) are both observed, wherein one type of objects are merely adhered to another, as shown in FIG. 3. As is understood in the above stated, in the composite A, two materials seem to be bonded to form a single material. When a single material consisting of hydroxyapatite is scanned for reference, finer crystal grains as compared to the composite A are clearly observed, so that one may suppose that it comprises collagen which is bonded with hydroxyapatite at gaps between crystallic structures.

From a further analysis of the above-mentioned composite, results shown in Table 2 are obtained.

TABLE 2

LOT: 61201M

| Analyzed and Tested Item | Result | Note | Method |
|---|---|---|---|
| Water Content | 4.2 g/100 g | | Heat Drying Method at Atmospheric Pressure |
| Collagen | 20.4 g/100 g | 1 | Kjeldahl Method |
| Sodium | 390 mg/100 g | | Atomic Absorption Spectroscopy |
| Phosphorus | 14.2 g/100 g | | ICP-Emission Spectrometry |
| Hydroxyapatite | 70.2 g/100 g | 2 | ICP-Emission Spectrometry |
| Magnesium | 323 mg/100 g | | ICP-Emission Spectrometry |
| pH | 6.6 | 3 | Glass Electrode Method |

Note 1. nitrogen-protein conversion factor: 6.25
Note 2. conversion factor from calcium: 2.5067
Note 3. measured based on 10% suspension As is seen in Table 2 above, the composite contains, as per 100 g, 4.2 g of water content (as measured by heat drying method at atmospheric pressure), 20.4 g of collagen (as measured by Kjeldahl method (nitrogen-protein conversion factor—6.25)), 14.2 g of phosphorus (as measured by ICP-emission spectrometry), 70.2 g of hydroxyapatite (as measured by ICP-emission spectrometry (conversion factor from calcium—2.5067)), 390 mg of sodium (as measured by atomic absorption spectroscopy), 323 mg of magnesium (as measured by ICP-emission spectrometry), and pH of the composite is 6.6 (as measured by glass electrode method (measured based on 10% suspension)). In the meantime, 28.0 g of calcium is identified by means of ICP-emission spectrometry in 70.2 g of hydroxyapatite. The calculation formula for determining the calcium content, 28.0 g, is as follows:

$$Ca_5(PO_4)_3OH = 5 \times 40.078 + 3 \times (30.973762 + 4 \times 15.9994) + 15.9994 + 1.00794$$

$$= 502.311426$$

Conversion Factor from Calcium $$Ca_5(PO_4)_3OH/(5 \times Ca) = 502.311426/(5 \times 40.078)$$
$$= 2.506669125 \rightarrow 2.5067$$

$$70.2/2.5067 \approx 28.0 \text{ g}$$

Moreover product standards for the composite are preferably those shown in Table 3 below. According to Table 3, it contains 10% or less of water (as measured by heat drying method at atmospheric pressure), 15% or more of collagen (as measured by Kjeldahl method (nitrogen-protein conversion factor—5.55)), 10% or more of phosphorus (as measured by ICP-emission spectrometry), 65% or more of hydroxyapatite (as measured by ICP-emission spectrometry (conversion factor from calcium—2.5067)), 0.5% or less of sodium (as measured by atomic absorption spectroscopy), 20 ppm or less of heavy metal (in form of Pb) (as measured by sodium sulfide colorimetric method), 2 ppm or less of arsenic (in form of $As_2O_3$) (as measured by atomic absorption spectroscopy), and of the composite is 6.0 to 8.0 (as measured by glass electrode method (measured based on 10% solution)), common bacteria count (viable cell count) is 3000 cells/g or less (as measured by standard agar culture method), coliform organisms are negative (as measured by BGLB method).

TABLE 3

Quality Standards

| Item | Standard Value | Test Method |
|---|---|---|
| Water Content | 10% or less | Heat Drying Method at Atmospheric Pressure |
| Collagen | 15% or more | Kjeldahl Method (Note 1) |
| Phosphorus | 10% or more | ICP-Emission Spectrometry |
| Hydroxyapatite | 65% or more | ICP-Emission Spectrometry (Note 2) |
| Sodium | 0.5% or less | Atomic Absorption Spectroscopy |
| pH | 6.0 to 8.0 | Glass Electrode Method (Note 3) |
| Heavy Metal (in form of Pb) | 20 ppm or less | Sodium Sulfide Colorimetric Method |
| Arsenic (in form of $As_2O_3$) | 2 ppm or less | Atomic Absorption Spectroscopy |
| Common Bacteria Count (Viable Cell Count) | 3000 cells/g or less | Standard Agar Culture Method |
| Coliform Organisms | Negative | BGLB Method |

(Note 1) nitrogen-protein conversion factor: 5.55
(Note 2) conversion factor from calcium: 2.5067
(Note 3) measured based on 10% solution Moreover, a study has been made for the effects of the composite obtained in the above-described manner on the bone improvements, in case of administration to osteoporotic model mice.

For study ICR female model mice of 10 weeks (of 20 g) were used. These mice underwent ovariectomy (OVX control group) and sham operation (sham operated group), and were subsequently fed with a conventional diet for 2 months, and then divided into 6 groups, each group having 10 mice. Of these, an OVX control group and a sham operated group were fed with 1.5 to 1.8% calcium containing feed which contained calcium carbonate as a calcium source. Further as a reference group, one group was treated with a bisphosphonate preparation (risedronate), which is an anti-osteoporotic agent showing obviously higher bone density. Remaining 3 groups were fed with special feeds, containing foodstuff and food additives. Combinations of foodstuff and food additives used in the present study are shown below in Table 4.

TABLE 4

| | | Drug Content |
|---|---|---|
| 1 | sham | None |
| 2 | OVX control | None |
| 3 | risedronate | 10 μg/10 μL/day at one dose |
| 4 | Vitamin $K_2$ (MK-4) | 500 μg/100 g of feed |
| 5 | Vitamin $K_2$ (MK-7) | 500 μg/100 g of feed |
| 6 | Composite | 2 g of Ca/100 g of feed |

After being fed these feeds for 2 months, mice were decapitated for blood collection. Then serum was separated from the collected blood, and after that calcium, phosphorus, and magnesium concentrations and alkaline phosphatase level of the serum were determined. Furthermore, after a resection of femurs, a three-dimensional bone densitometry and bone structure analysis were conducted on the femoral distal epiphyses and diaphyses, using pQCT (Peripheral Quantitative Computed Tomography) and μCT (micro focus X-ray CT).

For an analysis of the trabecular structure, three-dimensional image data of femoral distal epiphyses were acquired using X-ray μCT (MCT-CB130F, Hitachi Medico), of 8×8

μm focus, with micro focus X-ray tube. As conditions for imaging, tube voltage was 40 kV, tube current 100 μA, and voxel size 17.8×17.8×17.8 μm, so that 50 volume data for each were acquired. Three-dimensional images were reconstructed based on the acquired 50 two-dimensional images of a trabecular bone and a cortical bone. 3D parameters were then determined on these 3D images using trabecular structure measuring software (TRI/3D-BON; RATOC System Engineering, Co., Ltd). The determined structural parameters are listed below in Table 5.

TABLE 5

| | |
|---|---|
| BS/BV (1/mm) | Bone Surface Area |
| BV/BT (%) | Bone Mass per Tissue Volume (TV) |
| Tb · Th (mcm) | Trabecular Width |
| Tb · N (1/mm) | Trabecular Number |
| Tb · Sp. (mcm) | Trabecular Separation |
| Tb · Spac (mcm) | Trabecular Spacing |
| D | Complexity |
| TBPf (1/mm) | Trabecular Bone Pattern Factor |
| SMI | Structure Model Index |
| V * m.space | Marrow Space Star Volume |
| V * tr | Trabecular Star Volume |
| N · Nd | Number of Nodes |
| N · Tm | Number of Terminus |
| N · Ct | Number of Cortical Bones |
| N · Nd/TV (1/mm3) | Nodes per Tissue Volume (TV) |
| N · Tm/TV (1/mm3) | Terminus per Tissue Volume (TV) |
| N · Ct/TV | Cortical Bones per Tissue Volume (TV) |
| TSL | Total Trabecular Skeletal Length |
| NdNd/TSL (%) | Ratio of Node-to-Node Strut Length to Total Trabecular Skeletal Length |
| CtNd/TSL (%) | Ratio of Cortical Bone-to-Node Strut Length to Total Trabecular Skeletal Length |
| CtCt/TSL (%) | Ratio of Cortical Bone-to-Cortical Bone Strut Length to Total Trabecular Skeletal Length |
| TmTm/TSL (%) | Ratio of Terminus-to-Terminus Strut Length to Total Trabecular Skeletal Length |
| TSL/TV (1/mm2) | Total Trabecular Skeletal Length per Tissue Volume (TV) |
| NdNd/TV (1/mm2) | Node-to-Node Strut Length per Tissue Volume (TV) |
| CtNd/TV (1/mm2) | Cortical Bone-to-Node Strut Length per Tissue Volume (TV) |
| CtCt/TV | Cortical Bone-to-Cortical Bone Strut Length per Tissue Volume (TV) |
| TmTm/TV (1/mm2) | Terminus-to-Terminus Strut Length per Tissue Volume (TV) |

Student's t-test was used for statistical treatment for comparison between the groups. Only the parameters showing significant difference in the OVX control group are compared to those in the remaining groups.

Figure 6:
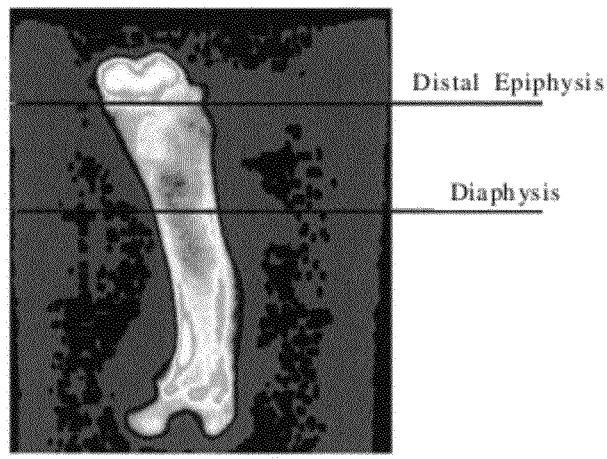
FIG. 6 is an explanatory view showing a femoral site for analysis, which is isolated from a model mouse.

Subsequently, a bone mass density (mg/cm³) as a physical quantity was analyzed separately for trabecular bones and cortical bones based on three-dimensional bone densitometry conducted using pQCT on the femoral distal epiphyses and diaphyses and cross-sectional images acquired in pQCT, and bone strength index was identified based on cortical bone width, second moment of area, and section modulus etc. Analyzed parameters are listed in Table 6. Student's t-test was used for statistical treatment for comparison between the groups. Sites designated for analysis are shown in FIG. 6.

TABLE 6

| ANALYZED PARAMETERS | | |
|---|---|---|
| Epiphyses | Bone Density | (mg/cm3) |
| | Trabecular Bone Density | (mg/cm3) |
| | Cortical Bone Density | (mg/cm3) |

TABLE 6-continued

| ANALYZED PARAMETERS | | |
|---|---|---|
| | Cortical Bone Cross-Section | (mm2) |
| | Cortical Bone Thickness | (mm) |
| | Periosteal Circumference | (mm) |
| | Bone Strength Index | (mm3) |
| Diaphyses | Bone Density | (mg/cm3) |
| | Trabecular Bone Density | (mg/cm3) |
| | Cortical Bone Density | (mg/cm3) |
| | Cortical Bone Cross-Section | (mm2) |
| | Cortical Bone Thickness | (mm) |
| | Periosteal Circumference | (mm) |
| | Bone Strength Index | (mm3) |

Subsequently, blood was collected from the tested mice of each group, and mineral concentration and ALP activity in serum were determined. Blood collection was conducted by decapitating under a twilight sleep. The collected blood stood for 1 hour at ice temperature, and thereafter the serum was separated by a centrifuge for 10 minutes at 1000 rpm. Calcium amount was determined by chelete coloring method. 50 μL of serum was added to 5 mL of a 0.88 M monoethanolamine buffer adjusted to pH=11, and a mixture of o-cresolphthalein complexone and 8-quinolinol as a coloring agent was further added. The resulting mixture was sufficiently stirred and stood for 5 minutes, and thereafter absorbance at 570 nm determined using a spectrometer. Phosphorus was determined by direct molybdenum blue method. After 0.2 mL of serum was added to 5 mL of a coloring agent and the resulting mixture stood for 15 minutes at room temperature, absorbance at 690 nm was determined using a spectrometer. The coloring agent was prepared by adding a surfactant to a mixture of ammonium molybdate, ammonium ferrous sulfate and sulfate. Magnesium was determined by xylidyl blue method. 3 mL of a coloring agent was added to 20 μL of serum and the resulting mixture stood for 10 minutes at room temperature, and thereafter absorbance at 520 nm was determined using a spectrometer. The coloring agent was prepared by adding a surfactant to a mixture of xylylazo violet I and ethylene glycol tetraacetic acid.

Alkaline phosphatase was determined by phenyl phosphoric acid substrate method. After 50 μL of serum was added to 2 mL of a substrate buffer and heated at 37° C. for 15 minutes, 2 mL of 36 mM potassium ferricyanide. The resulting mixture was sufficiently stirred, and thereafter absorbance at 570 nm was determined using a spectrometer. The substrate buffer was prepared by adding a mixture of 4-aminoantipyrine and phenylphosphoric acid to 50 mM carbonate buffer adjusted to pH=10.5.

In all of these determinations assay kits for clinical and biochemical use manufactured by Wako Pure Chemicals, Co., Ltd. were used.

TABLE 7

MINERAL CONCENTRATION AND ALP ACTIVITY IN MOUSE SERA

| | Ca (mg/dL) | P (mg/dL) | Mg (mg/dL) | ALP (BL unit) |
|---|---|---|---|---|
| 1. sham | 9.13 ± 1.02 | 7.02 ± 0.72 | 3.10 ± 1.05 | 3.88 ± 1.54 |
| 2. OVX | 9.00 ± 0.32 | 7.01 ± 0.78 | 2.72 ± 0.72 | 4.26 ± 1.98 |
| 3. Risedronate | 9.02 ± 1.15 | 6.95 ± 0.32 | 3.12 ± 1.21 | 3.65 ± 1.26 |
| 4. MK-4 | 9.60 ± 0.51 | 6.96 ± 0.44 | 2.67 ± 0.28 | 3.52 ± 1.82 |
| 5. MK-7 | 9.34 ± 1.50 | 7.12 ± 0.64 | 2.63 ± 0.63 | 3.77 ± 1.76 |
| 6. Composite | 9.80 ± 1.64 | 7.06 ± 0.76 | 2.71 ± 0.92 | 3.44 ± 1.59 |

Table 7 above shows mineral concentrations and alkaline phosphatase (ALP) activity in model mouse sera. As per blood Ca, P and Mg, no significant difference could not be observed between all the tested groups. On the other hand, concerning ALP activity which shows high rate in presence of bone metabolic abnormalities, no significant difference was observed in the present test results, although all groups tended to show low rates as compared to the OVX control group.

Table 8 below shows a significant difference comparison between a OVX control group and tested groups in femoral distal epiphyses and femoral distal diaphyses which were measured by pQCT. In the OVX control group and a sham operated group 11 parameters showed a significant difference, which demonstrated that the OVX control group obviously consisted of osteoporotic model mice. Moreover, a group treated with risedronate which is an anti-osteoporotic agent showed a significant increase in bone density, trabecular bone density, cortical bone thickness and cortical bone cross-section of the epiphyses, and in cortical bone thickness and cortical bone cross-section of the diaphyses, as compared to the OVX control group. In this manner an effect of risedronate characterized in a bone density increase was proven, which demonstrated that the present test was conducted with high precision. Further, among the tested groups, a composite group showed the most similar effect to the group treated with risedronate. In the meantime, MK7 showed a more significant increase in cortical bone thickness, cortical bone cross-section, periosteal circumference and bone strength index of the femoral distal epiphyses, as compared to the OVX control group. However, in the diaphyses, no significant difference is observed as compared to the OVX control group. In addition, in MK4 group only an epiphyseal periosteal circumference significantly increased as compared to the OVX control group.

TABLE 8

| | | OVX | sham | Risedronate | Composite | MK4 | MK7 |
|---|---|---|---|---|---|---|---|
| Epiphyses | Bone Density (mg/cm3) | | p < 0.01 | p < 0.01 | | | |
| | Trabecular Bone Density (mg/cm3) | | p < 0.05 | p < 0.05 | | | |
| | Cortical Bone Density (mg/cm3) | | p < 0.01 | | p < 0.01 | | |
| | Cortical Bone Cross-Section (mm2) | | p < 0.01 | p < 0.05 | p < 0.05 | | p < 0.05 |
| | Cortical Bone Thickness (mm) | | p < 0.01 | p < 0.05 | p < 0.05 | | p < 0.05 |
| | Periosteal Circumference (mm) | | | | | p < 0.05 | p < 0.01 |
| | Bone Strength Index (mm3) | | p < 0.05 | | p < 0.01 | | p < 0.05 |
| Diaphyses | Bone Density (mg/cm3) | | p < 0.01 | | | | |
| | Trabecular Bone Density (mg/cm3) | | p < 0.05 | | p < 0.05 | p < 0.05 | |
| | Cortical Bone Density (mg/cm3) | | p < 0.01 | | p < 0.05 | | |
| | Cortical Bone Cross-Section (mm2) | | p < 0.01 | p < 0.05 | | | |
| | Cortical Bone Thickness (mm) | | p < 0.01 | p < 0.05 | | | |
| | Periosteal Circumference (mm) | | | | | | |
| | Bone Strength Index (mm3) | | | | | | |
| Items showing a significant difference | | | 11 | 6 | 6 | 2 | 4 |

Figure 7:
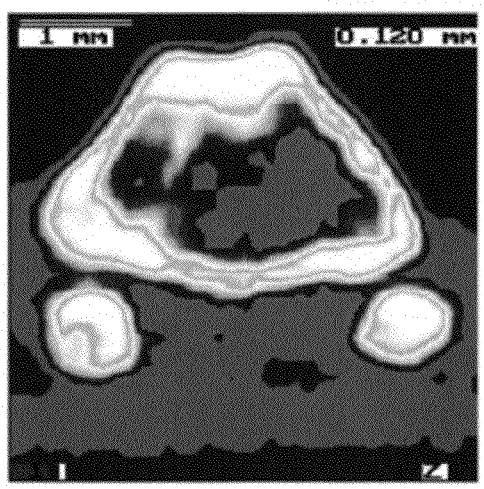
FIG. 7 is a pQCT image of the site for analysis, in OVX control model mice and those treated with a composite which is manufactured according to the present invention.
Figure 7:
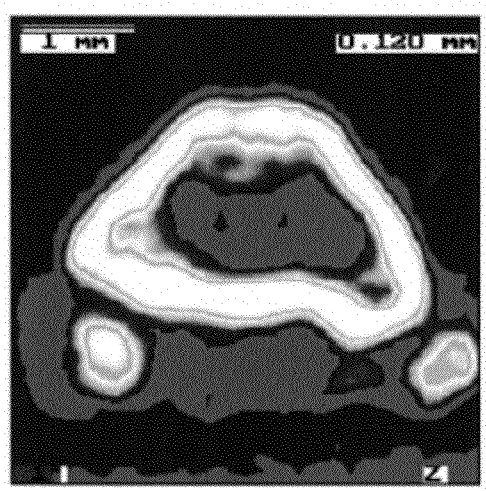
Figure 7:
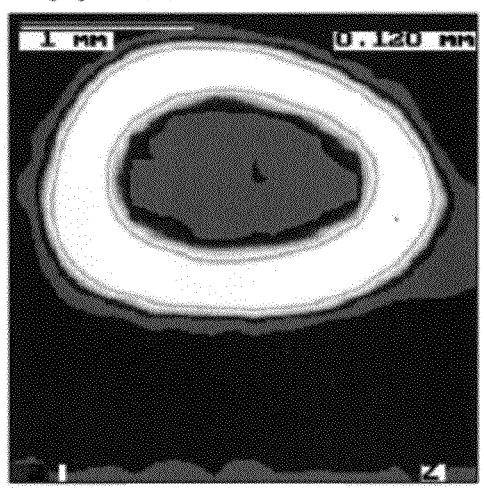
Figure 7:
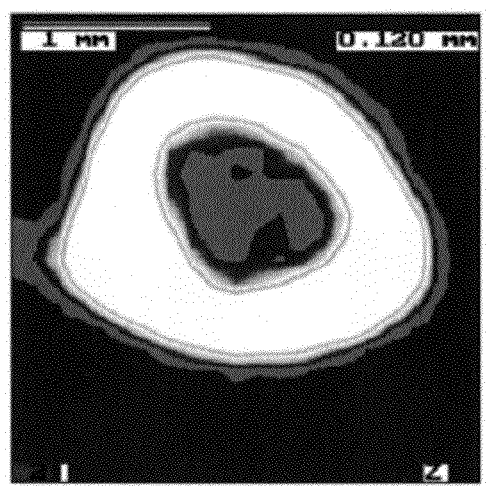

FIG. 7 shows representative pQCT images of an OVX control group and a composite group, on femoral distal epiphyses (A) and diaphyses (B) of model mouse. An area in white represents a cortical bone, while areas inside and outside is trabecular bones. The cortical bone had more thickness in a mouse treated with the composite, which enabled to visually confirm a rise in bone density.

Table 9 below shows results of a three-dimensional structure analysis of bone internal structure of model mouse using µCT in femoral distal epiphyses. Parameters of the tested groups in the bold-bordered cells showed higher means than those of the OVX control group, which demonstrated better effects on improvement of bone internal structure. On the other hand, parameters in the cells without bold borders showed lower means than those of the OVX control group, and lower the means, better the effects on improvement of bone internal structure. In other words, if Tb.SP, TB space, TBPf, VmSpace, N.Tm, TmTm/TSL, TmTm/TV show a lower value, they show better effects on improvement of bone internal structure. A sham operated group showed significant effects on improvement of trabecular bone structure concerning 11 parameters, while a risedronate group concerning 12, which demonstrated that the present experimental system was implemented with high precision. After these, MK7, the composite and MK4 is arranged in this order according to the importance of the effects on improvement of trabecular bone structure

TABLE 9

| | Measured Items | OVX | sham | Risedronate | Composite | MK4 | MK7 |
|---|---|---|---|---|---|---|---|
| BS/BV | Bone Surface Area | | | | | | |
| BV/TV | Bone Mass per Tissue Volume (TV) | | $p < 0.01$ | $p < 0.01$ | | | $p < 0.05$ |
| Tb. Th | Trabecular Width | | | | | | |
| TB. N | Trabecular Number | | $p < 0.01$ | $p < 0.01$ | $p < 0.05$ | $p < 0.05$ | $p < 0.01$ |
| Tb. Sp. | Trabecular Separation | | $p < 0.01$ | $p < 0.01$ | $p < 0.05$ | $p < 0.05$ | $p < 0.01$ |
| Tb. Spac | Trabecular Spacing | | $p < 0.01$ | $p < 0.01$ | $p < 0.05$ | $p < 0.05$ | $p < 0.01$ |
| D | Complexity | | | $p < 0.05$ | | | |
| TBPf | Trabecular Bone Pattern Factor | | | | $p < 0.05$ | | |
| SMI | Structure Model Index | | | | | $p < 0.05$ | |
| V*m. space | Marrow Space Star Volume | | $p < 0.01$ | $p < 0.01$ | | | |
| V*tr | Trabecular Star Volume | | $p < 0.05$ | | | | |
| N. Nd | Number of Nodes | | | | | | $p < 0.05$ |
| N. Tm | Number of Terminus | | | | | | |
| N. Ct | Number of Cortical Bones | | $p < 0.05$ | $p < 0.01$ | | | $p < 0.01$ |
| N. Nd/TV | Nodes per Tissue Volume (TV) | | | | | | |
| N. Tm/TV | Terminus per Tissue Volume (TV) | | | | | | |
| N. Ct/TV | Conical Bones per Tissue-Volume (TV) | | $p < 0.05$ | $p < 0.01$ | | | $p < 0.01$ |
| TSL | Total Trabecular Skeletal Length | | $p < 0.05$ | $p < 0.01$ | $p < 0.05$ | | $p < 0.01$ |
| NdNd/TSL | Ratio of Node-to-Node Strut Length to Total Trabecular Skeletal Length | | | | | | |
| CtNd/TSL | Ratio of Cortical Bone-lo-Node Strut Length to Total Trabecular Skeletal Length | | | | | | |
| CtCt/TSL | Ratio of Cortical Bone-to-Cortical Bone Strut Length to Total Trabecular Skeletal Length | | | | | | |
| TmTm/TSL | Ratio of Terminus-to-Terminus Strut Length to Total Trabecular Skeletal Length | | | | $p < 0.01$ | | $p < 0.05$ |
| TSL/TV | Total Trabecular Skeletal Length per Tissue Volume (TV) | | $p < 0.05$ | $p < 0.01$ | $p < 0.05$ | | $p < 0.05$ |
| NdNd/TV | Node-to-Node Strut Length per Tissue Volume (TV) | | | | | | |
| CtNd/TV | Cortical Bone-to-Node Strut Length per Tissue Volume (TV) | | $p < 0.01$ | $p < 0.01$ | $p < 0.05$ | | $p < 0.01$ |
| CtCt/TV | Cortical Bone-to-Cortical Bone Strut Length per Tissue Volume (TV) | | | | | | |
| TmTm/TV | Terminus-to-Terminus Strut Length per Tissue Volume (TV) | | | $p < 0.01$ | | | |
| | Items showing a significant difference | | 11 | 12 | 8 | 4 | 11 |

Figure 8:
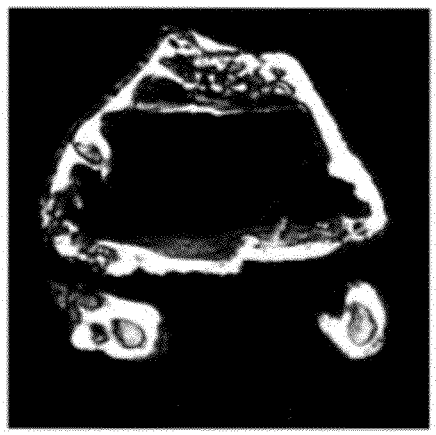
FIG. 8 is a 3-D image of trabecular structure in OVX control model mice and sham operated ones, in traverse and a longitudinal cross section.
Figure 8:
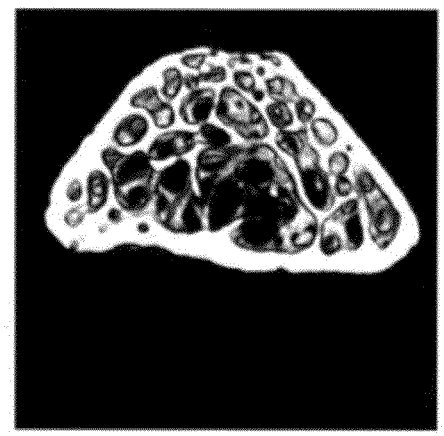
Figure 8:
Figure 8:
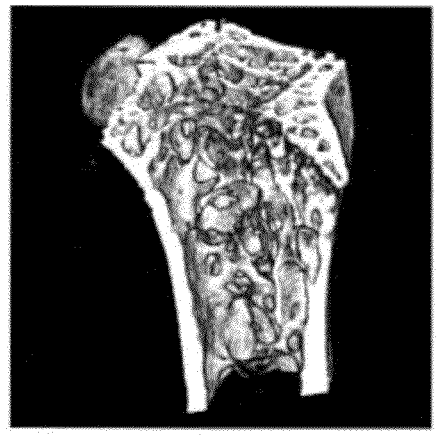
Figure 9:
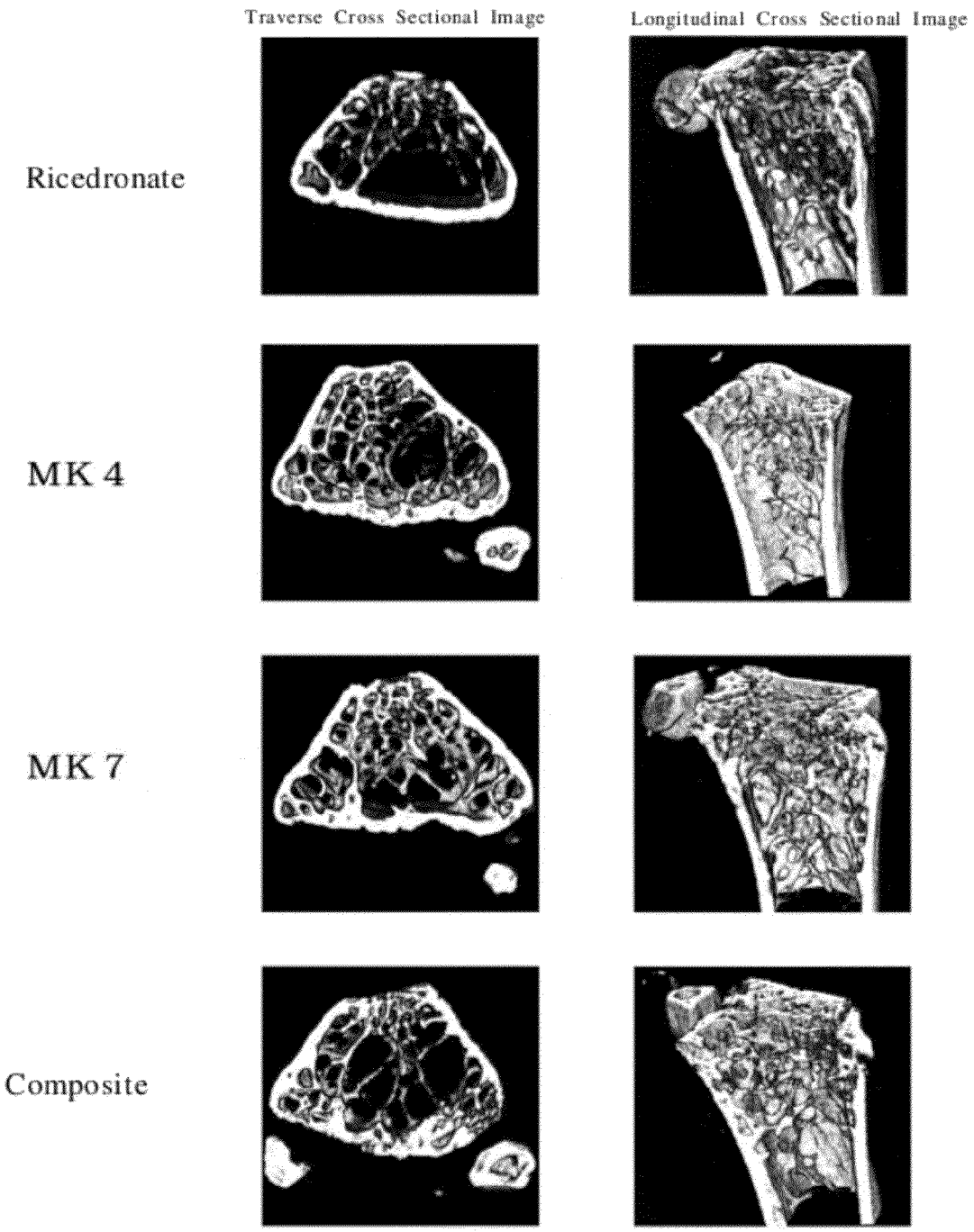
FIG. 9 is a 3-D image of trabecular structure in model mice treated by risedronate, MK4, MK7 and a composite which is manufactured according to the present invention, in a cross section and a longitudinal section.

FIG. 8 shows 3-D restructured images of representative trabecular structure of an OVX control group and a sham operated group in transverse and longitudinal cross-sections. FIG. 9 equally shows 3-D restructured images of representative trabecular structure of a risedronate group, a MK4 group, a MK7 group and a composite group in transverse and longitudinal cross-sections.

As described in detail in the foregoing, as a result of the 3-D image analysis conducted using OVX mice in distal epiphyses and diaphyses for effects on an improvement of bone density and trabecular structure, based on images shown in FIGS. 8 and 9, the following conclusions were drawn:

1. The composite showed both effects on an increased bone density and improved trabecular structure, with the increase in bone density being a prevalent effect. Moreover, merely the composite showed an increase in diaphyseal cortical bone density.

2. MK7 showed both effects on an increased bone density and improved trabecular structure, with the improvement in trabecular structure being prevalent effect.

3. For MK4 an improvement in bone internal structure was observed as a prevalent effect.

From the effects listed above it is evident that the composite shows a marked effect on an increased bone density, with an improvement in bone internal structure being further expected, thus the composite is effective in prevention for osteoporosis and improvement for a deteriorated bone structure.

As described in the forgoing, a hydroxyapatite/collagen composite forming a biocompatible material according to the present invention has almost no odor and taste, proves safe as it is made of fish scales, and has an excellent in effect on bone quality improvement. Therefore, it is clear that the composite is useful to improve and prevent various diseases and symptoms due to calcium deficiency including osteoporosis, by taking it as is or mixed with other foodstuff, confectionery, chewing gum, drinking water, etc. Moreover, the process for producing the composite can be incorporated into those for producing a fish scale-derived hydroxyapatite or collagen, which enables an easy manufacture.

What is claimed is:

1. A process for producing a biocompatible composite material, the method comprising:
   mixing (i) a first fish scale extract, said first extract comprising hydroxyapatite and having 70 to 75% (w/w) water content with (ii) a second fish scale extract, said second extract comprising collagen and having 40 to 60% (w/w) water content, thereby forming a mixture and wherein the hydroxyapatite:collagen weight percentage ratio in the mixture is about 8:2;
   stirring the mixture; and
   drying the mixture using a hot blast, thereby producing said biocompatible composite material.

2. The process for producing the biocompatible material according to claim 1, wherein the producing of the composite is incorporated in a process for producing the fish scale-obtained hydroxyapatite.

3. The process for producing the biocompatible material according to claim 1, wherein the producing of the composite is incorporated in the process for producing the fish scale-obtained collagen.

* * * * *